United States Patent [19]

Goldstein

[11] Patent Number: 4,491,411

[45] Date of Patent: Jan. 1, 1985

[54] EXPLORATION METHOD FOR FINDING URANIUM ORE BODIES

[75] Inventor: Theodore Goldstein, Yardley, Pa.

[73] Assignee: Mobil Oil Corporation, New York, N.Y.

[21] Appl. No.: 392,824

[22] Filed: Jun. 28, 1982

[51] Int. Cl.³ ............................................. G01N 21/55
[52] U.S. Cl. ........................................ 356/30; 250/253
[58] Field of Search .................. 250/253, 256; 356/30, 356/445

[56] References Cited

U.S. PATENT DOCUMENTS 4,030,837  6/1977  Kojima et al. .................. 356/445
4,267,445  5/1981  Cabbiness et al. .............. 250/255

FOREIGN PATENT DOCUMENTS 505945  3/1976  U.S.S.R. ......................... 356/30

Primary Examiner—Janice A. Howell
Assistant Examiner—Constantine Hannaher
Attorney, Agent, or Firm—A. J. McKillop; Michael G. Gilman; Charles A. Malone

[57] ABSTRACT

The migration of a uranium ore body through geologic time may be determined by subjecting the carbonaceous material in host rock to vitrinite reflectance analysis. A substantial variation in the reflectance is an indication of anomalous coalification induced by radiation from uranium ore.

37 Claims, No Drawings

EXPLORATION METHOD FOR FINDING URANIUM ORE BODIES

BACKGROUND OF THE INVENTION

This invention relates to locating uranium ore bodies. More particularly, it relates to a method of analyzing host rocks for radiation induced changes which can indicate the location of uranium ore bodies. This invention especially relates to the tracking of the migration of uranium ore bodies through geologic time by detecting radiation induced changes in organic matter associated with sedimentary deposits.

The location of mineral ore deposits has been of concern to mankind for centuries. A variety of techniques has been developed to locate and analyze deposits of economically important mineral ores. In many instances the deposit itself has to be located before a particular exploration procedure can effectively be employed. Samples of an ore have been obtained by drilling into the earth and removing a core sample for physical and chemical analysis. Geologging, electric logging and ultrasonic logging have been used for years in locating oil, natural gas and coal. More recently, gamma ray and neutron logging have proven successful in oil, gas and coal exploration. These procedures have also been employed with varying degrees of success in locating metal ore deposits.

Exploration techniques which can be successfully employed in the field without the requirement of collecting samples for later laboratory analysis are particularly preferred. One such procedure is described in South Africa patent application no. 80-3732 of Scintrex Limited which relates to a method for the detection of certain minerals of uranium, zinc, lead and other metals using photoluminescence. This method may be employed in the field and selectively rejects the fluorescent response of the abundant photoluminescent rocks and substances which occur at the surface of the earth while detecting the fluorescent response of a mineral of economic significance having a lifetime of photoluminescence between 1 and 500 microseconds through consideration of their differences in photoluminescent lifetimes.

Uranium ore deposits, because of their radioactive nature, may be easier to locate than other metal ores. However, one still must be in close proximity to a uranium ore deposit before detecting its radioactivity. Low grade deposits of uranium ore are widely distributed throughout the world and many have been found since some countries are willing to pay the cost of production from these deposits. On the other hand, higher-grade deposits are far less plentiful but some have been located. Those in the United States, Canada, France, and South Africa are among the principal ones which supply uranium ore to the free world. Locating high grade deposits of uranium ore which can be commercially developed remains an economically attractive venture.

Many sedimentary uranium ore bodies are continually mobilized, through geologic time, by ground waters moving through the sedimentary formation. As the ground waters move through the sediment, the ore body is gradually moved downstream by a process of solubilization and reprecipitation. Sometime in the geologic past, of course, these uranium ore bodies were located upstream from their present day location.

Because uranium minerals are radioactive, they produce radiation induced changes in sediments that contain them. As a uranium ore body is mobilized through a sediment, the host rocks are exposed to the radiation in the vicinity of the ore body. But while the ore body is moved downstream through the sedimentary strata, most other components of the host rock (e.g., sand grains, insoluble organic matter, etc.) are not. As a result, the mobilized ore body leaves a radiation induced signature or trail of its past positions.

Examination of likely host rocks for radiation induced changes can guide the explorationist in finding uranium ore bodies. If a radiation signature is observed in a sediment, but no uranium, the ore body will be found downstream. If there is no radiation signature, either the ore body is upstream, or there is no ore body in that part of the sediment.

It is an object of this invention to provide a method for finding uranium ore bodies.

It is another object of this invention to provide a method for analyzing host rocks to detect radiation induced changes in the rocks which have been caused by uranium ore deposits.

It is further object of this invention to detect uranium ore deposits by an indirect procedure.

The achievement of these and other objects will be apparent from the following description of the subject invention.

SUMMARY OF THE INVENTION

In accordance with the present invention, it has been found that vitrinite reflectance analysis of the organic material of core or cutting samples to determine coal rank can indicate radiation induced changes caused by uranium ore bodies formerly associated with the organic material.

In particular, this invention relates to a method of locating a uranium ore body by tracking the migration of said body through geologic time which comprises:

(a) determining the coal rank of the carbonaceous material in a sample of host rock by subjecting said material to vitrinite reflectance analysis in at least two locations on the face of said material, and (b) comparing the vitrinite reflectance data to determine if substantial variations in the vitrinite reflectance data from the said at least two locations exists to indicate different coal rank within said material.

DESCRIPTION OF THE PREFERRED EMBODIMENTS

The present invention relates to tracking the migration of uranium ore bodies through geologic time by examining organic deposits found in core or cutting samples for radiation induced changes. Specifically, the present invention relates to an exploration method of determining the presence of a uranium ore body in the vicinity of the location of interest by determining if the organic deposit in a core sample contains coalified particles of different rank in the same granule. Since such granules, in the same sample would rarely occur in the absence of radiation, the determination of substantially different coal ranks in the same granule is a strong indication that the organic material was in close proximity to a uranium ore body at some time in its geologic history. Radiation, such as that from a body of uranium ore, will accelerate the coalification process, causing coalified particles of substantially different ranks in a particular organic deposit. The terms, "organic" and "carbonaceous" are used herein interchangeably and refer to the material being subjected to vitrinite reflectance analysis.

One way to recognize the past association of uranium minerals with a sedimentary rock involves examination of the organic matter present in the sedimment. Sedimentary organic matter will undergo anomalous coalification induced by radioactive materials such as uranium minerals. The anomalous coalification can be recognized by petrographic techniques including vitrinite reflectance measurements.

Coals form a continuous metamorphic series from peat to graphite. The progressive increase of coal rank (coalification, in the language of coal technology) results from the integrated effects of temperature and time on the coal, i.e., the integrated thermal exposure. The vitrinite reflectance technique was devised by coal petrologists as a method for determining rank of coals. Vitrinite, deriving from the woody tissues of higher plants, is one of three main classes of constituents (macerals) composing coal. It is a prominent and often dominant constituent of humic coals. The two other maceral classes are exinite, consisting of more lipid-rich entities such as pollen and spore exines, algal bodies, leaf cuticles, etc., and inertinite, consisting of highly altered woody tissues (fusinite) and strongly decomposed plant detritus (micrinite).

A vitrinite reflectance analysis of a coal specimen first requires preparation of a polished thin section of coal. The section is examined by reflected light microscopy, and vitrinite is identified visually. The quantity measured is the percent of incident light that is reflected by the surface of the vitrinite grains or lenses within the coal. There is some natural variation from grain to grain so a statistical average is sought by making 50 to 100 individual measurements. There is a sensitive spot, $3\mu$ in diameter, centered on the cross hairs, and the reflectance (in percent) of any entity that is brought under the cross hairs can be photometrically measured. Individual measurements are automatically recorded on paper tape, and data on all 50-100 grains can be fed to a computer for analysis and plotting. The data are customarily plotted in the form of a frequency diagram or histogram. For example, a sample of coal was analyzed by vitrinite reflectance. One hundred grains of vitrinite were measured in this specimen. The relative number of measurements that fell in each 0.05% interval was plotted on a histogram. The mean reflectance, designated $R_o$, was 0.77 percent in this specimen. $R_o$ is the quantity used to characterize the vitrinite reflectance of a coal. Individual measurements as low as 0.60 percent and as high as 0.95 percent occurred here. The spread of the distribution is indicated by the standard deviation, sigma, which in this case was 0.08. The probability is 0.68 that an individual measurement will fall within $0.77 \pm 0.08$. Of more significance is the accuracy of replication if the entire distribution were re-measured. This accuracy is indicated by $0.77 \pm 0.02$ and is the 95% confidence interval. This indicates that approximately 95 times out of 100 a re-measurement would yield a mean reflectance, $R_o$, between 0.75 and 0.79. One can see that $R_o$ can be determined quite precisely in a coal specimen even though there may be considerable spread in the reflectance from discrete grains of vitrinite. In utilizing $R_o$ values to establish coal rank, the higher the $R_o$ value, the higher the rank of the sample.

Although coals are excellent specimens to use for paleotemperature determinations where they are available, they are too sparsely distributed in most sedimentary sections to be of general use. The burgeoning application of the reflectance method by industry is occurring because it has been found that the method can also be applied to the dispersed organic matter of sedimentary rocks. Vitrinite, deriving from plant fragments (phytoclasts), is generally present as a constituent of the organic matter (kerogen) of sedimentary rocks which is insoluble in organic solvents. In coals, vitrinite can range up to 100% of the total organic matter. In terrestrial sediments, vitrinite may constitute more than 50% of the total kerogen. In marine sediments, it is generally much less abundant, and becomes sparser with increasing distance from shore. In deep ocean sediments it may constitute much less than 1% of the total kerogen. However, even here one can usually find a statistically significant number of phytoclasts to measure.

Whether it is present in coal or in dispersed organic matter of sedimentary rocks, vitrinite increases in reflectance with increasing thermal exposure. Radiation induced changes in organic material will cause anomalous $R_o$ values.

In one application of the method of this invention, samples of a likely sedimentary host rock are obtained by drilling. Either core or cutting samples can be used, but cores are preferred. The sediments are examined by standard petrographic techniques, and the vitrinite reflectance of the organic matter determined. Evidence of radiation induced anomalous coalification indicates the existence of a uranium ore body in the sediment. This radiation signature is followed to the present day location of the ore body.

The vitrinite reflectance of the carbonaceous material of interest must be measured in at least two locations to determine if the material is of significantly different coal rank. A measurement at the periphery and in the center of the sample should provide sufficient data in most instances. Where additional data are required, a traverse from the periphery to the center with vitrinite reflectance measurements made at from 2 to 6 locations should suffice. Where the several locations on the sample face show substantial variation in vitrinite reflectance of between about 0.5 and 1.5%, this is sufficient to show a significant difference in coal rank within the sample.

Where the vitrinite reflectance results show significantly different coal rank within a sample, this is anomalous and is an indication that a uranium ore body at sometime in geologic time was in close proximity to the organic materials. Since the host rock and associated organic material have not migrated with time to the extent that uranium ore is capable, the task of the skilled geologist is to track the uranium ore body to its present location. Further vitrinite reflectance analysis of likely host rocks in the vicinity will assist in locating the uranium ore body. Where no radiation induced changes are found the ore body is upstream of this site. Where the coal rank is significantly different, the uranium ore will be found downstream of the sample site. Continuing in this fashion, the skilled artisan can track the uranium ore body to its present location.

The following example demonstrates the practice of the invention.

A sample of uranium ore containing a layer of coaly organic matter was obtained from the Kerr-McGee mine at Ambrosia Lake, New Mexico.

The ore sample consisted of a layer of dull, black organic matter cemented to a dark sandstone fragment. The sandstone, except for a light grey streak along one face, was uniformly dark and easily crushed. The organic matter appeared to be somewhat laminar and could be chipped or sawed.

Both the sandstone and the organic portion of the specimen were anlayzed for uranium. The sandstone was found to contain 5 wt.% uranium and the organic matter 16 wt.% uranium.

A portion of the organic matter, cut normal to the bedding plane, was examined. The sample was "coal by definition" since it was possible to recognize some plant tissues microscopically.

A 1 cm fragment of the organic material was polished and the vitrinite reflectance was determined by reflected light microscopy. At the periphery of the sample the coal rank was the highest ($R_o \approx 2\%$) while in the center of the sample it was the lowest ($R_o \approx 0.5\%$). The coal rank varied from anthracite to sub-bituminous.

An elemental analysis of the organic matter showed that the sample contained 42.91% C, 2.93% H, 36.65% ash, and 17.5% O,N,S (by difference). The atomic C/H ratio of this material is 0.8, a value roughly half-way between anthracite coal (0.5) and peat (ca 1.1).

From these data, it can be seen that unlike most woody materials that undergo gradual but uniform coalification on burial, the coal rank of the organic portion of the sample varied widely. This variation in coal rank can be attributed to radiation changes induced by the uranium ore associated with the organic matter during the geologic past.

Organic matter in sediments can be instrumental in concentrating and mineralizing certain types of ore bodies. According to this genetic mechanism, highly functionalized organic matter (e.g., humic and woody matter, sub-bituminous coal, etc.) present in the host rock concentrates water soluble hexavalent uranium species by ion exchange reactions. The organic matter can also serve as a reductant in the conversion of hexavalent uranium to insoluble tetravalent minerals.

There is geologic evidence to suggest that the organic matter was emplaced in the sandstone sediments of the area from where the sample was obtained prior to the introduction of the uranium. If the organic matter was somewhat particular, it might be expected that ion exchange reactions with soluble uranium species would occur first at the exposed exchange sites near the surface of the particle and much later, if at all, with deeply buried sites. In this process the highest concentration of uranium would be found at the periphery of the particle. It should be noted that the coal rank of the organic matter in the above specimen was highest at the periphery of individual fragments and lowest towards their centers.

What is claimed is:

1. A method for determining the existence of uranium containing ore bodies by vitrinite reflectance measurements of organic deposits or material contained in a coal, sedimentary rock or other similar material comprising the steps of:
   (a) obtaining and preparing a sample of the coal, sedimentary rock, or other similar material which sample is suitable for making vitrinite reflectance measurements;
   (b) measuring vitrinite reflectance from at least two locations on the face of said sample; and
   (c) recording substantial variations in said vitrinite reflectance measurements emitted from the face of said sample which variations represent the existence of different ranks of coal which indicates that a uranium ore body was in close proximity to said organic deposit.

2. The method as recited in claim 1 where in step (b) reflectance measurements are obtained from the periphery and the center of said sample.

3. The method as recited in claim 1 where in step (b) said reflectance measurements are obtained by a traverse from the periphery to the center of said sample at from about 2 to about 6 locations.

4. The method as recited in claim 1 where in step (c) substantial variations of vitrinite reflectance are between about 0.5 and 1.5%.

5. The method as recited in claim 1 where in step (b) the vitrinite reflectance is determined by reflected light microscopy.

6. The method as recited in claim 1 where in step (c) said coal rank varies from anthracite to sub-bituminous.

7. The method as recited in claim 1 where an elemental analysis is used to confirm the existence of coals of different rank as shown by a variation in the atomic carbon and hydrogen ratio.

8. The method as recited in claim 1 where in step (c) the variation in coal rank is attributable to radiation changes induced by said uranium ore associated with the organic matter during the geologic past.

9. The method as recited in claim 1 where an analysis of the organic portion of said sample is used to conform the existence of uranium.

10. The method as recited in claim 1 where the coal rank of the organic matter in said sample is highest at the periphery of individual fragments and lowest towards their centers indicative of a high concentration of uranium at the periphery of the fragment.

11. The method as recited in claim 1 where in step (c) individual measurements are automatically recorded on paper tape.

12. The method as recited in claim 1 where in step (c) data on from about 50 to about 100 grains or fragments are fed into a computer for analysis and plotting.

13. The method as recited in claim 12 where the data are plotted in the form of a frequency diagram or histogram.

14. A method for locating a uranium containing ore body by vitrinite reflectance measurements of organic deposits or material contained in a coal, sedimentary rock, or other similar material comprising the steps of:
   (a) obtaining a sample of said coal, sedimentary rock, or other similar material from a location or site of interest;
   (b) determining the existence of coalified particles of different rank in at least one granule obtained from said sample by vitrinite reflectance measurements which indicates that said organic material was in close proximity to a uranium ore body at some time in its geologic history;
   (c) obtaining other samples of said coal, sedimentary rock, or other similar material in the vicinity of said location or site; and
   (d) determining the existence of coalified particles with a coal rank significantly different from the coalified particles in step (b) by vitrinite reflectance measurements which indicates that the uranium ore body will be found downstream of said site;
   (e) choosing a new location or site of interest downstream of said site; and
   (f) repeating steps (a) and (d) until the uranium ore body is tracked to its present location.

15. The method as recited in claim 14 where in step (b) reflectance measurements are obtained from the periphery and the center of said sample.

16. The method as recited in claim 14 where in step (b) said reflectance measurements are obtained by a traverse from the periphery to the center of said sample at from about 2 to about 6 locations.

17. The method as recited in claim 14 where in step (b) said vitrinite reflectance is determined by reflected light microscopy.

18. The method as recited in claim 14 where in step (b) said coal rank varies from anthracite to sub-bituminous.

19. The method as recited in claim 14 where in step (b) an elemental analysis is used to confirm the existence of coals of different rank as shown by a variation in the atomic carbon and hydrogen ratio.

20. The method as recited in claim 14 where in step (b) the variation in coal rank is attributable to radiation changes induced by said uranium ore associated with the organic matter during the geologic past.

21. The method as recited in claim 14 where an analysis of said organic portion of said sample is used to conform the existence of uranium.

22. The method as recited in claim 20 where the coal rank of said organic matter in said sample is highest at the periphery of individual granules or fragments and lowest towards their centers indicative of a high concentration of uranium at the periphery of the fragments.

23. The method as recited in claim 14 where in step (b) individual measurements are automatically recorded on paper tape.

24. The method as recited in claim 14 where in step (b) where data on from about 50 to about 100 grains, particles or fragments are fed into a computer for analysis and plotting.

25. The method as recited in claim 24 where the data are plotted in the form of a frequency diagram or histogram.

26. A method for locating a uranium containing ore body by vitrinite reflectance measurements of organic deposits or material contained in a coal, sedimentary rock, or other similar material comprising the steps of:
    (a) obtaining a sample of said coal, sedimentary rock, or other similar material from a location or site of interest;
    (b) determining the existence of coalified particles of different rank in at least one granule obtained from said sample by vitrinite reflectance measurements which indicates that said organic material was in close proximity to a uranium ore body at some time in its geologic history;
    (c) obtaining other samples of said coal, sedimentary rock, or other similar material in the vicinity of said location or site;
    (d) determining from the sample obtained from step (c) that no radiation induced changes exist which indicates that the uranium ore body will be found upstream of said sample site;
    (e) choosing a new location or site of interest upstream of said site; and
    (f) repeating the sampling and determination steps until said uranium ore body is tracked to its present location.

27. The method as recited in claim 26 where in step (b) said reflectance measurements are obtained from the periphery and the center of said sample.

28. The method as recited in claim 26 where in step (b) said reflectance measurements are obtained by a traverse from the periphery to the center of said sample at from about 2 to about 6 locations.

29. The method as recited in claim 26 where in step (b) said vitrinite reflectance is determined by reflected light microscopy.

30. The method as recited in claim 26 where in step (b) said coal rank varies from anthracite to sub-bituminous.

31. The method as recited in claim 26 where an elemental analysis is used to confirm the existence of coals of different rank as shown by a variation in the atomic carbon and hydrogen ratio.

32. The method as recited in claim 26 where in step (b) the variation in coal rank is attributable to radiation changes induced by said uranium ore associated with the organic matter during the geologic past.

33. The method as recited in claim 26 where an analysis of said organic portion of said sample is used to confirm the existence of uranium.

34. The method as recited in claim 33 where the coal rank of said organic matter in said sample is highest at the periphery of individual fragments and lowest towards their centers indicative of a high concentration of uranium at the periphery of the fragment.

35. The method as recited in claim 26 where in step (b) individual measurements are automatically recorded on paper tape.

36. The method as recited in claim 26 where in step (b) said data on from about 50 to about 100 grains, particles or fragments are fed into a computer for analysis and plotting.

37. The method as recited in claim 36 where the data are plotted in the form of a frequency diagram or histogram.

* * * * *